(12) United States Patent
Osaka

(10) Patent No.: US 7,174,278 B2
(45) Date of Patent: Feb. 6, 2007

(54) ANALYZER AND INFORMATION MANAGEMENT METHOD OF THE SAME

(75) Inventor: Naoki Osaka, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 10/998,417

(22) Filed: Nov. 29, 2004

(65) Prior Publication Data
US 2005/0125200 A1    Jun. 9, 2005

(30) Foreign Application Priority Data
Dec. 8, 2003    (JP) .............................. 2003-409332

(51) Int. Cl.
*G06F 11/00* (2006.01)

(52) U.S. Cl. ..................... 702/188; 709/224

(58) Field of Classification Search ........ 702/120–122, 702/186, 188; 709/224; 714/4, 47
See application file for complete search history.

(56) References Cited

U.S. PATENT DOCUMENTS

| | | | |
|---|---|---|---|
| 6,286,050 B1 * | 9/2001 | Pullen et al. ............... | 709/229 |
| 6,557,026 B1 * | 4/2003 | Stephens, Jr. ............... | 709/203 |
| 6,754,854 B2 * | 6/2004 | Kurrasch ...................... | 714/47 |
| 6,819,655 B1 * | 11/2004 | Gregson ...................... | 370/242 |
| 6,954,720 B2 * | 10/2005 | Oya ........................... | 702/188 |
| 2004/0249836 A1 * | 12/2004 | Reynders et al. ........... | 707/100 |

* cited by examiner

*Primary Examiner*—Marc S. Hoff
*Assistant Examiner*—Mary Catherine Baran
(74) *Attorney, Agent, or Firm*—Rankin, Hill, Porter & Clark LLP

(57) ABSTRACT

A controller of each liquid chromatograph includes: a management information collector for collecting and retaining management information on each section included in the liquid chromatograph; a first terminal for transmitting/receiving the information in the management information collector to/from an external device, the first terminal including a network interface for managing analyzers as a first interface; an analyzer controller for controlling an analysis operation of the liquid chromatograph and collecting/retaining analysis information; and a second terminal for transmitting/receiving the information in the analyzer controller to/from a PC as an external device, the second terminal provided separately from the first terminal and including a control interface for controlling analyzers provided separately from the network interface for managing analyzers.

5 Claims, 4 Drawing Sheets

ANALYZER AND INFORMATION MANAGEMENT METHOD OF THE SAME

BACKGROUND OF THE INVENTION

1. Field of the Invention

The present invention relates to an analyzer such as a liquid chromatograph and a mass spectroscope, and a method for managing information on the analyzer.

2. Description of the Related Art

An analyzer such as a liquid chromatograph requires important management information for managing the analyzer, on top of the important analysis information such as analysis conditions and analysis data. The management information includes a device number (analyzer number), status information such as under analysis, analysis end and standby state, as well as exhaustion such as the service life of the source light of an optical detector, if any, and the result of operation check.

The analyzer is equipped with terminals for external connection, such as an RS-232C, GP-IB, and ETHERNET (R). The analyzer uses one of the terminals to connect to a personal computer (PC). To use a plurality of terminals of an analyzer, the format of data transmitted/received on a terminal is sometimes processed for transmission/reception on another terminal. In such a case where an analyzer is connected to a network, the analysis information and management information are displayed on the analyzer as well as on an external device connected to the network such as a PC. This allows the information to be obtained externally to the analyzer.

The analysis information and management information are transmitted/received on the same terminal. When information is transmitted/received while the analyzer is connected to an external device such as a PC, the same PC can be used to obtain both analysis information and management information.

The related art teaches analyzers where analysis information and management information are transmitted/received on the same terminal and have a risk of information leakage. For example, leakage of analysis information, as well as management information, can occur when management of the analyzer is subcontracted to an external agent. This presents a problem with the safety of information management.

SUMMARY OF THE INVENTION

It is an object of the present invention to provide an analyzer capable of safely managing the information on the analyzer.

To achieve this objective, the invention includes the following configuration.

An analyzer according to the invention comprises:

a management information collector for collecting and retaining management information on each section of the analyzer;

a first terminal for transmitting/receiving the information in the management information collector to/from an external device, the first terminal including a first interface as a network interface;

an analyzer controller for controlling an analysis operation of the analyzer and collecting and retaining analysis information; and a second terminal for transmitting/receiving the information in the analyzer controller to/from an external device, the second terminal provided separately from the first terminal and including a second interface provided separately from the first interface.

The second interface can also be a network interface.

The management information includes the device number (analyzer number), status information (under analysis, analysis end and standby state), exhaustion of a part such as the source light of the detector, and the result of operation check.

The analysis information includes the detection result by the analyzer, instruction of analysis operation, and analysis conditions.

A method for managing information of the above-mentioned analyzer according to the invention comprises:

connecting the first terminal and the second terminal of the analyzer to a separate network or external device; and independently transmitting/receiving the management information and the analysis information.

In case a plurality of analyzers are used, the first terminal of each of the analyzers is connected to a common first network and the second terminal of each of the analyzers is connected to a common external device or a common second network other than the first network.

An interface is provided for transmitting/receiving analysis information separately from an interface for transmitting/receiving management information to/from outside, and the respective interfaces are externally connected via separate terminals. Thus, the interfaces can be connected to separate network or external device to allow respective information to be transmitted/received independently. This upgrades the safety of information management.

DETAILED DESCRIPTION OF THE INVENTION

Figure 1:
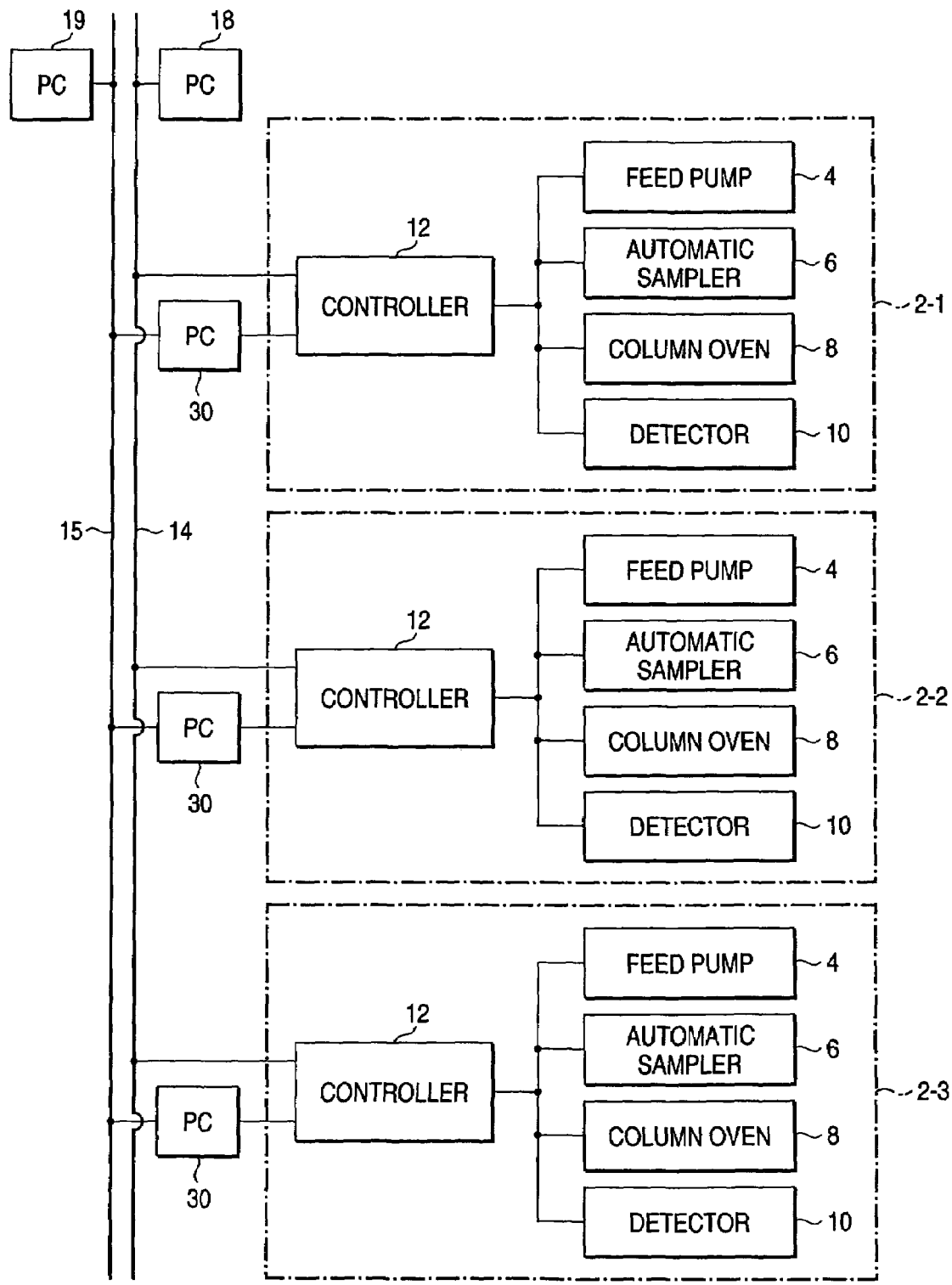
FIG. 1 is a schematic view of an embodiment of a liquid chromatograph connected to a network.
Figure 2:
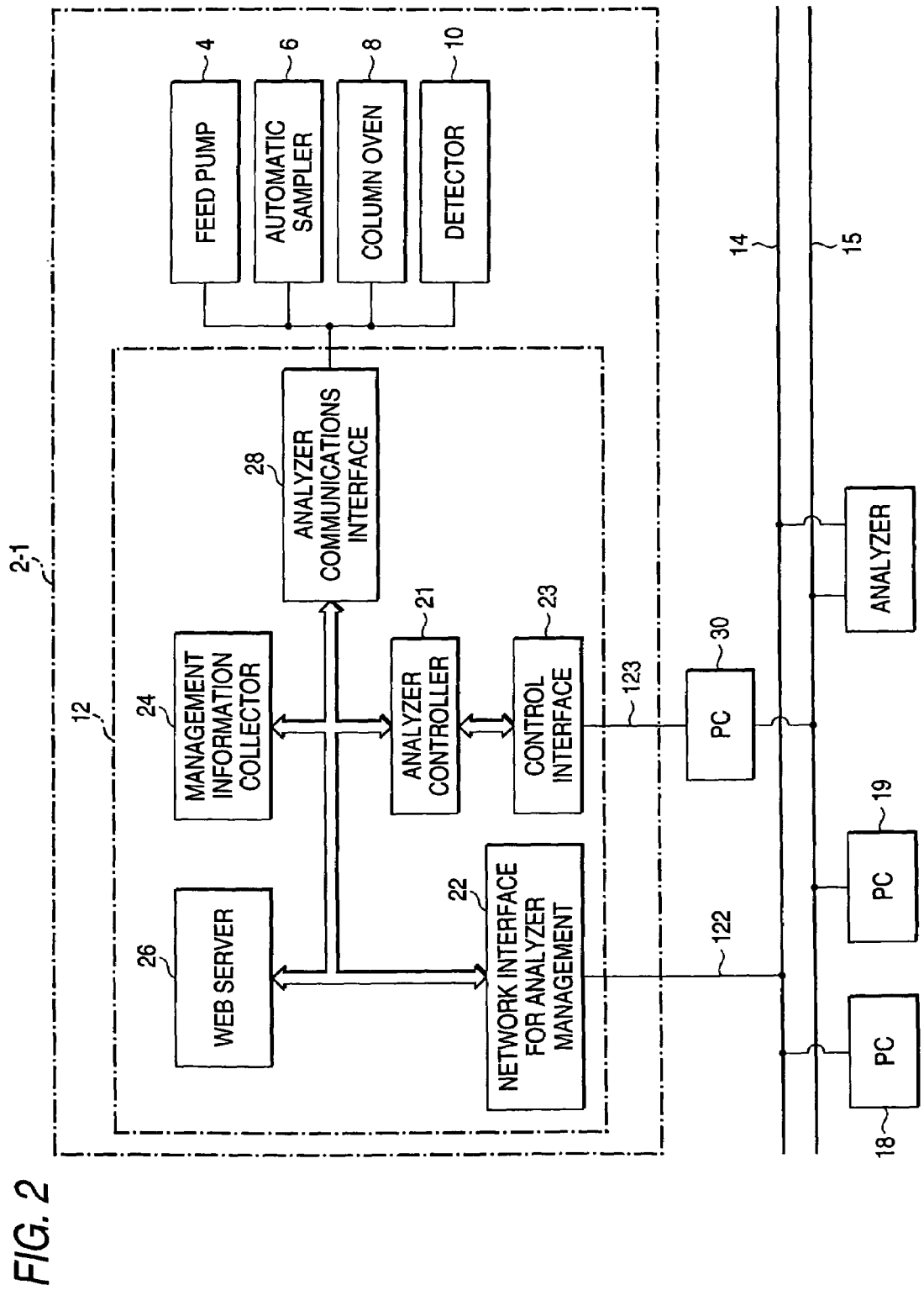
FIG. 2 is a block diagram showing the details of the function of a controller in one liquid chromatograph of the embodiment.

FIGS. 1 and 2 show an embodiment of the invention. FIG. 1 is a block diagram which schematically shows the state where liquid chromatographs 2-1 through 2-3 are connected as analyzers to a network. FIG. 2 shows the details of a controller 12 in one liquid chromatograph 2-1 shown in FIG. 1. The controller 12 is implemented by a CPU (Central Processing Unit).

The liquid chromatographs 2-1 through 2-3 have the same configuration. Each of the liquid chromatographs 2-1 through 2-3 function as a unit to perform the analysis and are comprised a feed pump 4 for delivering an eluant to a column, a column oven 8 including the column for separating sample components, an automatic sampler 6 for injecting a sample into the flow path of the eluant delivered to the column by the feed pump 4, and a detector 10 for detecting sample components eluted from the column.

Each of the liquid chromatographs 2-1 through 2-3 is equipped with a controller 12. The controller 12 comprises: a management information collector 24; a first terminal 122;

an analyzer controller 21; and a second terminal 123. The management information collector 24 collects and retains management information on each section included in the liquid chromatograph. The first terminal 122 transmits/receives the information in the management information collector 24 to/from an external device. The first terminal 122 includes a network interface 22 for managing analyzers (hereinafter referred to as network interface for analyzer management) as a first interface. The analyzer controller 21 is for controlling the analysis operation of the liquid chromatograph and collecting/retaining analysis information. The second terminal 123 transmits/receives information in the analyzer controller 21 to/from a PC 30 as an external device. The second terminal 123 is provided separately from the first terminal 122 and includes an interface 23 for controlling the analyzer (hereinafter referred to as control interface) as a second interface provided separately from the network interface 22 for analyzer management as the first interface.

The network interface 22 for analyzer management as the first interface can be directly connected to a network 14 via the first terminal 122, and provide the information in the management information collector 24 to a browser (PC) 18 as a network client via the network 14 by way of a web server 26. The network interface 22 for analyzer management is connected to the management information collector 24 and transmits/receives to/from the network 14 the information collected in the management information collector 24. This information would include, for example, the device number of the liquid chromatograph, status information, exhaustion of parts, and the result of operation check.

In this embodiment, the control interface 23 is not a network interface, so that its terminal 123 can be connected to a network 15 via the PC 30. The control interface 23 is connected to the analyzer controller 21 and transmits/receives to/from the network 15 the information collected in the analyzer controller 21 such as the detection result of the detector 10 included in the liquid chromatograph.

The controller 12 further comprises: an analyzer communications interface 28; and a web server 26 as a network server. The analyzer communications interface 28 controls the analysis operation of the liquid chromatograph under instructions from the analyzer controller 21 and the management information collector 24, collects the detection result (analysis information) obtained by the detector, and collects the management information on the liquid chromatograph. The management information collector 24 collects management information such as the operating state of the liquid chromatograph and its user as well as management information on the feed pump 4, automatic sampler 6, column oven 8 and detector 10 included in the liquid chromatograph as individual information via the analyzer communications interface 28. The analyzer controller 21 controls the feed pump 4, automatic sampler 6, column oven 8 and detector 10 included in the liquid chromatograph in correspondence with the analysis conditions and collects via the analyzer communications interface 28 the analysis result such as the detection result in the detector 10.

The network 14 is a network for transmitting management information and the network 15 is one for transmitting analysis information. In addition to the liquid chromatographs 2-1 through 2-3, an analyzer having the characteristics of the invention may be connected to the networks 14, 15. A PC 18 is connected to the network 14. The PC 18 comprises a browser such as Internet Explorer. The PC 18 can thus detect management information such as that on the liquid chromatographs 2-1 through 2-3 connected to the network 14. APC 19 is connected to the network 15. The PC 19 can thus detect analysis results (analysis data) in the liquid chromatographs 2-1 through 2-3 connected to the network 15.

Now, the operation of the embodiment will be described taking the liquid chromatograph 2-1 as an example.

The management information collector 24 collects, as required, the management information such as a device number, status information and exhaustion of parts. The management information includes information other than the analysis information on the feed pump 4, automatic sampler 6, column oven 8 and detector 10.

The PC 18 including a browser, searches for a controller of the analyzers connected to the network 14 such as the liquid chromatographs 2-2, 2-3 and requests management information on an arbitrary analyzer. The PC 19 including a browser, searches for a controller of the analyzers connected to the network 15 such as the liquid chromatographs 2-2, 2-3 and requests analysis information on an arbitrary analyzer or issues an instruction concerning analysis conditions to an arbitrary analyzer.

Receiving a request for information from the PC 18 or 19 including a browser, the web server 29 transmits information to the PC 18 or 19 via the network interface 22 for analyzer management or control interface 23. This operation is the same for the liquid chromatographs 2-2 and 2-3.

Figure 3:
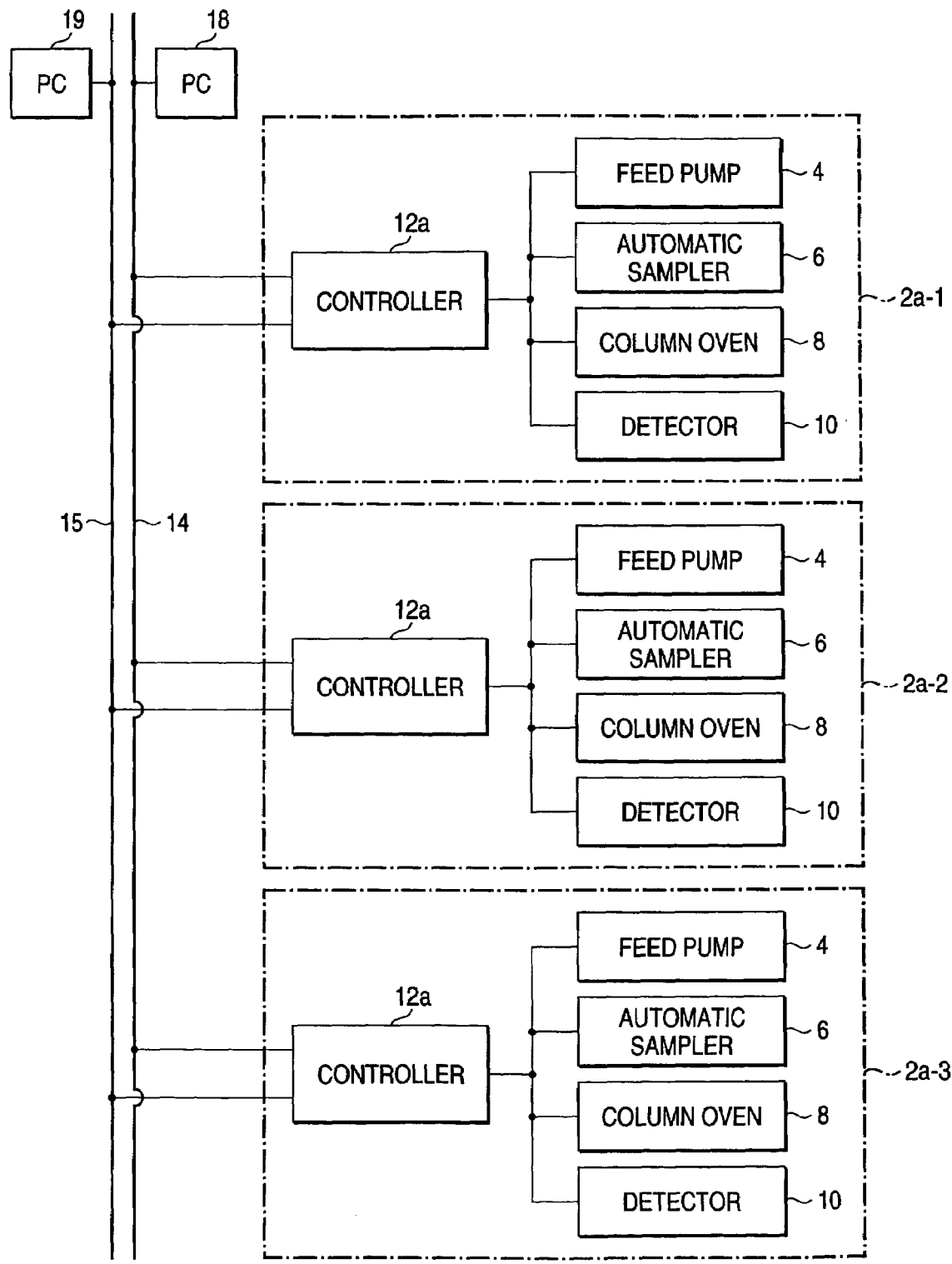
FIG. 3 is a schematic view of another embodiment of a liquid chromatograph connected to a network.
Figure 4:
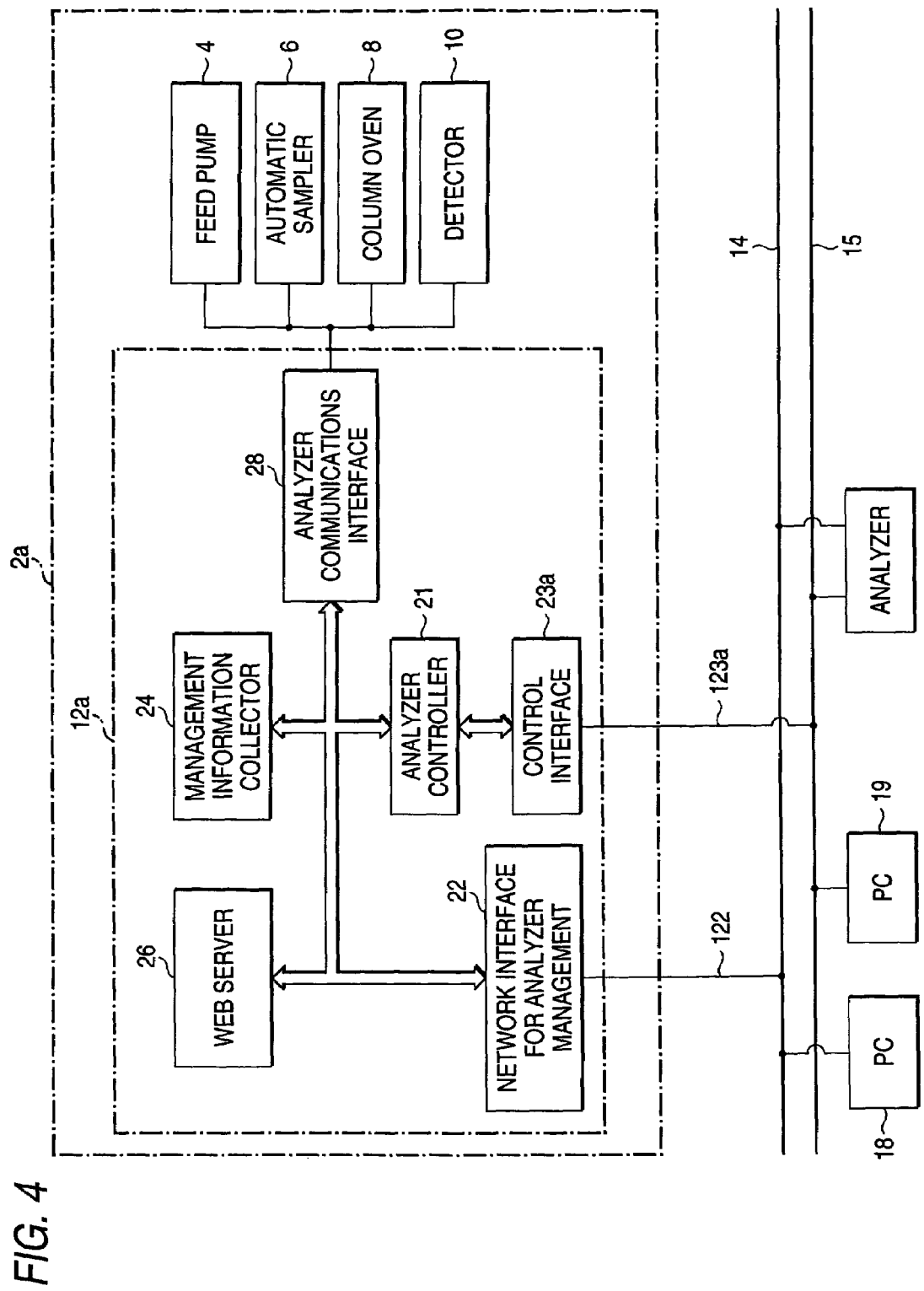
FIG. 4 is a block diagram showing the details of the function of a controller in one liquid chromatograph of the embodiment.

FIGS. 3 and 4 show another embodiment of the invention. FIG. 3 is a block diagram which schematically shows the state where liquid chromatographs 2a-1 through 2a-3 are connected as analyzers to a network. FIG. 4 shows the details of the function of a controller 12a in one liquid chromatograph 2a-1 shown in FIG. 3.

This embodiment is different from the first embodiment shown in FIGS. 1 and 2 in that a control interface 23a is also a network interface. As a result, a terminal 123a can be directly connected to the network 15 and transmit/receive, by way of the web server 26, information collected by the analyzer controller 21 such as the detection result of the detector 10 included in the liquid chromatograph.

The other configuration and functions are same as those of the first embodiment, so detailed description is omitted.

With a related art analyzer, for example, in case a manager of the analyzer, other than an analyst, uses a browser to check the management information on the analyzer, the manager may access the information such as the analysis conditions and analysis result on the same browser. This presented a problem with the safety of information management. According to the invention, only management information is accessible on the PC 18 and the analysis conditions and analysis result are inaccessible. This enhances the safety of information management.

What is claimed is:

1. An analytical instrument comprising:
   a management information collector for collecting and retaining management information on each section of the analytical instrument;
   a first port for transmitting/receiving the information in said management information collector to and from a first external device, said first port including a first interface as a network interface;
   an analytical instrument controller for controlling an analysis operation of the analytical instrument and collecting and retaining analysis information; and
   a second port for transmitting/receiving the information in said analytical instrument controller to and from a second external device, said second port being provided separately from said first port and including a second interface provided separately from the first interface.

2. The analytical instrument according to claim 1, wherein said second interface is also a network interface.

3. A method for managing information on an analytical instrument, the method comprising:
   providing the analytical instrument comprising:
      a management information collector for collecting and retaining management information on each section of the analytical instrument;
      a first port for transmitting/receiving the information in said management information collector to and from a first external device, said first Port including a first interface as a network interface;
      an analytical instrument controller for controlling an analysis operation of the analytical instrument and collecting and retaining analysis information; and
      a second port for transmitting/receiving the information in said analytical instrument controller to and from a second external device, said second port being provided separately from said first port and including a second interface provided separately from the first interface;
   connecting the first port to one of a first network and the first external device;
   connecting the second port to one of a second network and the second external device, said second network being different than said first network and said second external device being different than said first external device;
   transmitting/receiving management information via the first port; and
   transmitting/receiving analysis information via the second port and independently of the transmitting/receiving of management information via the first port.

4. A method for managing information on a plurality of analytical instruments, comprising the steps of:
   providing the analytical instruments, each analytical instrument comprising:
      a management information collector for collecting and retaining management information on each section of the analytical instrument;
      a first port for transmitting/receiving the information in said management information collector to and from a first external device, said first port including a first interface as a network interface;
      an analytical instrument controller for controlling an analysis operation of the analytical instrument and collecting and retaining analysis information; and
      a second port for transmitting/receiving the information in said analytical instrument controller to and from a second external device, said second port being provided separately from said first port and including a second interface provided separately from the first interface;
   connecting the first port of each analytical instrument to a common first network; and
   connecting the second port of each analytical instrument to one of a common external device and a common second network, said common second network being different than said common first network.

5. The method according to claim 4, comprising the further steps of:
   transmitting/receiving management information via the first port of each analytical instrument; and
   transmitting/receiving analysis information via the second port of each analytical instrument and independently of the transmitting/receiving of management information via the first port.

* * * * *